15# United States Patent [19]

Beckett et al.

[11] Patent Number: 5,840,939
[45] Date of Patent: Nov. 24, 1998

[54] DERIVATIVES OF SUCCINAMIDE AND THEIR USE AS METALLOPROTEINASE INHIBITORS

[75] Inventors: Raymond Paul Beckett; Andrew Miller; Zoe Marie Spavold; Mark Whittaker, all of Oxford, United Kingdom

[73] Assignee: British Biotech Pharmaceuticals, Ltd., England

[21] Appl. No.: 930,619

[22] PCT Filed: Apr. 18, 1996

[86] PCT No.: PCT/GB96/00930

§ 371 Date: Oct. 7, 1997

§ 102(e) Date: Oct. 7, 1997

[87] PCT Pub. No.: WO96/33161

PCT Pub. Date: Oct. 24, 1996

[30] Foreign Application Priority Data

Apr. 18, 1995 [GB] United Kingdom ............... 9507799

[51] Int. Cl.⁶ ............... C07C 231/00; C07C 229/00; A61K 31/16
[52] U.S. Cl. ............... 554/37; 562/441; 562/623
[58] Field of Search ............... 562/441, 623; 554/37

[56] References Cited

FOREIGN PATENT DOCUMENTS 9410990  5/1994  WIPO .

*Primary Examiner*—Gary Geist
*Assistant Examiner*—Brian J. Davis
*Attorney, Agent, or Firm*—Banner & Witcoff, Ltd.

[57] ABSTRACT

Compounds of formula (I), wherein X is a —$CO_2H$ or —CONHOH group;

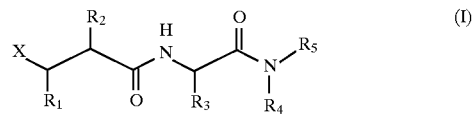

$R_4$ is a group —$CHR^xR^y$ wherein $R^x$ and $R^y$ independently represent optionally substituted phenyl or monocyclic heteroaryl rings, which optionally may be linked covalently to each other by a bond or by a $C_1$–$C_4$ alkylene or $C_2$–$C_4$ alkenylene bridge; and $R_1$, $R_2$, $R_3$ and $R_5$ as defined in the specification are selective inhibitors of stromelysin-1 and matrilysin relative to human fibroblast collagenase and 72 KDa gelatinase.

16 Claims, No Drawings

DERIVATIVES OF SUCCINAMIDE AND THEIR USE AS METALLOPROTEINASE INHIBITORS

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation. Some of the compounds of the invention are, in addition, inhibitors of the release of tumour necrosis factor from cells.

BACKGROUND TO THE INVENTION

Compounds which have the property of inhibiting the action of metalloproteinases involved in connective tissue breakdown such as collagenases, stromelysins and/or gelatinases (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas.

Metalloproteinases are characterised by the presence in the structure of a zinc(II) ionic site. It is now known that there exists a range of metalloproteinase enzymes that includes human fibroblast collagenase (Type 1), PMN-collagenase, 72 kDa-gelatinase, 92 kDa-gelatinase, stromelysin-1, stromelysin-2 and PUMP-1 (J. F. Woessner, FASEB J, 1991, 5, 2145–2154). Many known MMP inhibitors are peptide derivatives, based on naturally occuring amino acids, and are analogues of the cleavage site in the collagen molecule. A paper by Chapman et. al. (J. Med. Chem. 1993, 36, 4293–4301) reports some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the zinc(II) site in the MMP, and known classes include those in which the zinc binding group is a hydroxamic acid, carboxylic acid, sulphydryl, and oxygenated phosphorus (eg phosphinic acid and phosphonamidate including aminophosphonic acid) groups.

Two known classes of pseudopeptide or peptide mimetic MMP inhibitors have a hydroxamic acid group and a carboxylic group respectively as their zinc binding groups. With a few exceptions, such known MMPs may be represented by the structural formula (I)

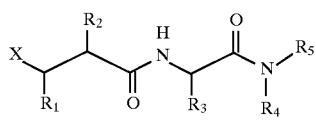

in which X is the zinc binding hydroxamic acid (—CONHOH) or carboxylic acid (—COOH) group and the groups $R_1$ to $R_5$ are variable in accordance with the specific prior art disclosures of such compounds. Examples of patent publications disclosing such structures are given below.

In such compounds, it is generally understood in the art that variation of the zinc binding group and the substituents $R_1$, $R_2$ and $R_3$ can have an appreciable effect on the relative inhibition of the metalloproteinase enzymes. The group X is thought to interact with metalloproteinase enzymes by binding to a zinc(II) ion in the active site. Generally the hydroxamic acid group is preferred over the carboxylic acid group in terms of inhibitory activity against the various metalloproteinase enzymes. However, the carboxylic acid group in combination with other substituents can provide selective inhibition of gelatinase (EP-489,577-A). The $R_1$, $R_2$ and $R_3$ groups are believed to occupy respectively the P1, P1' and P2' amino acid side chain binding sites for the natural enzyme substrate. There is evidence that a larger $R_1$ substituent can enhance activity against stromelysin, and that a $(C_1$–$C_6)$alkyl group (such as isobutyl) at $R_2$ may be preferred for activity against collagenase whilst a phenylalkyl group (such as phenylpropyl) at $R_2$ may provide selectivity for gelatinase over the other metalloproteinases.

Tumour necrosis factor (herein referred to as "TNF") is a cytokine which is produced initially as a cell-associated 28 kD precursor. It is released as an active, 17 kD form, which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

As mentioned above, MMP inhibitors have been proposed with hydroxamic acid or carboxylic acid zinc binding groups. The following patent publications disclose hydroxamic acid-based and/or carboxylic acid-based MMP inhibitors:

U.S. Pat. No. 4,599,361 (Searle)
EP-A-0236872 (Roche)
EP-A-0274453 (Bellon)
WO 90/05716 (British Bio-technology)
WO 90/05719 (British Bio-technology)

WO 91/02716 (British Bio-technology)
EP-A-0489577 (Celltech)
EP-A-0489579 (Celltech)
EP-A-0497192 (Roche)
WO 92/13831 (British Bio-technology)
WO 92/17460 (SmithKline Beecham)
WO 92/22523 (Research Corporation Technologies)
WO 93/09090 (Yamanouchi)
WO 93/09097 (Sankyo)
WO 93/20047 (British Bio-technology)
WO 93/24449 (Celltech)
WO 93/24475 (Celltech)
EP-A-0574758 (Roche)
EP-A-0575844 (Roche)
WO 94/02446 (British Biotech)
WO 94/02447 (British Biotech)
WO 94/21612 (Otsuka)
WO 94/21625 (British Biotech)
WO 94/24140 (British Biotech)
WO 94/25434 (Celltech)
WO 94/25435 (Celltech)
WO 95/04033 (Celltech)
WO 95/04735 (Syntex)
WO 95/04715 (Kanebo)

BRIEF DESCRIPTION OF THE INVENTION

This invention makes available a class of compounds of formula (I) above wherein X is a hydroxamic acid or carboxylic acid group characterised primarily in that the $R_4$ substituent is a group —$CHR^xR^y$ wherein $R^x$ and $R^y$ independently represent optionally substituted phenyl or monocyclic heteroaryl rings, which optionally may be linked covalently to each other by a bond or by a $C_1$–$C_4$ alkylene or $C_2$–$C_4$ alkenylene bridge.

DETAILED DESCRIPTION OF THE INVENTION

The present invention provides compounds of general formula I

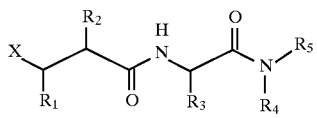

wherein

X is —$CO_2H$ or —CONHOH group;

$R_1$ is hydrogen;

$R_2$ is a ($C_1$–$C_6$)alkyl, ($C_2$–$C_6$)alkenyl, ($C_2$–$C_6$)alkynyl, phenyl($C_1$–$C_6$)alkyl, heteroaryl($C_1$–$C_6$)alkyl, cycloalkyl($C_1$–$C_6$)alkyl or cycloalkenyl($C_1$–$C_6$) alkyl group, any one of which may be optionally substituted by one or more substituents selected from ($C_1$–$C_6$) alkyl, —O($C_1$–$C_6$)alkyl, —S($C_1$–$C_6$)alkyl, —$OCH_2Ph$ wherein the phenyl group may be optionally substituted, halo and cyano (—CN);

$R_3$ is the characterising group of a natural or non-natural α amino acid in which any functional groups may be protected;

$R_4$ is a group —$CHR^xR^y$ wherein $R^x$ and $R^y$ independently represent optionally substituted phenyl or monocyclic heteroaryl rings, which optionally may be linked covalently to each other by a bond or by a $C_1$–$C_4$ alkylene or $C_2$–$C_4$ alkenylene bridge, either of which may be optionally interrupted by an O or S atom;

$R_5$ is hydrogen or a ($C_1$–$C_6$)alkyl group;

or a salt, hydrate or solvate thereof.

As used herein the term "($C_1$–$C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, pentyl and hexyl.

The term "$C_1$–$C_4$ alkylene bridge" means one of the following divalent moieties, namely —$CH_2$—, —$CH_2CH_2$—, —$CH_2CH_2CH_2$—, or —$CH_2CH_2CH_2CH_2$—.

The term "($C_2$–$C_6$)alkenyl" means a straight or branched chain alkenyl moiety having from 2 to 6 carbon atoms having at least one double bond of either E or Z stereochemistry where applicable. This term would include, for example, vinyl, allyl, 1- and 2-butenyl and 2-methyl-2-propenyl.

The term "$C_2$–$C_4$ alkenylene bridge" means one of the following divalent moieties, namely —CH=CH—, —CH=CHCH_2—, —$CH_2$CH=CH— or —CH=CHCH_2CH_2—, $CH_2$CH=CHCH_2—, —$CH_2CH_2$CH=CH—, or —CH=CHCH=CH—.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 4–8 carbon atoms and includes, for example, cyclohexenyl, cyclooctenyl, cycloheptenyl, cyclopentenyl, and cyclobutenyl. In the case of cycloalkenyl rings of from 5–8 carbon atoms, the ring may contain more than one double bond.

The unqualified term "heterocyclyl" or "heterocyclic" means (i) a 5-7 membered heterocyclic ring containing one or more heteroatoms selected from S, N and O, and optionally fused to a benzene ring, including for example, pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, or (ii) a naphththalimido (ie 1,3-dihydro-1,3-dioxo-2H-benz[f] isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

The term "monocyclic heteroaryl" means a 5-7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with up to four substituents, each of which independently may be ($C_1$–$C_6$)alkyl, ($C_1$–$C_6$) alkoxy, hydroxy, mercapto, ($C_1$–$C_6$)alkylthio, amino, halo (including fluoro, chloro, bromo and iodo), nitro, trifluoromethyl, —COOH, —$CONH_2$, —CN, —$COOR^A$ or —$CONHR^AR^A$ wherein $R^A$ is a ($C_1$–$C_6$)alkyl group or the residue of a natural alpha-amino acid.

The term "characterising group of a natural alpha-amino acid" means the characteristic side chain attached to the —CH(NH$_2$)(COOH) moiety in the following amino acids: glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. In this context, protected amino groups include amido and acylamino, protected hydroxy or mercapto groups include ethers and thioethers, protected carboxyl groups include esters, and imidazolyl, indolyl or guanidyl groups may be protected as t-butoxycarbonyl derivatives. These are only examples of the many protecting derivatives known in the art, and others will be known to the skilled man.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the $R_1$ and X groups—S,
C atom carrying the $R_2$ group—R,
C atom carrying the $R_3$ group—S,
C atom carrying the $R^x$ and $R^y$ groups—R or S but mixtures in which the above configurations predominate are also contemplated.

As previously stated, the compounds of the invention are principally distinguished from the compounds disclosed in the prior art patent publications listed above by the identity of the group $R_4$. Accordingly, the groups $R_1$, $R_2$, $R_3$, and $R_5$ may be any of the groups which have been disclosed in the corresponding positions of compounds disclosed in any of those prior art patent publications listed above. Without limiting the generality of the foregoing, the following classes of substituent $R_3$ have been disclosed in the corresponding position of prior art compounds, and are therefore suitable $R_3$ groups for use in compounds of the present invention:

($C_1$–$C_6$)alkyl, benzyl, hydroxybenzyl, benzyloxybenzyl, ($C_1$–$C_6$)alkoxybenzyl, or benzyloxy($C_1$–$C_6$)alkyl group; and the characterising group of a natural α amino acid, in which any functional group may be protected, any amino group may be acylated and any carboxyl group present may be amidated; and a group —[Alk]$_n$R$_6$ where Alk is a ($C_1$–$C_6$)alkyl or ($C_2$–$C_6$)alkenyl group optionally interrupted by one or more —O—, or —S— atoms or —N(R$_7$)— groups [where R$_7$ is a hydrogen atom or a ($C_1$–$C_6$)alkyl group], n is 0 or 1, and R$_6$ is an optionally substituted cycloalkyl or cycloalkenyl group; and a benzyl group substituted in the phenyl ring by a group of formula —OCH$_2$COR$_8$ where R$_8$ is hydroxyl, amino, ($C_1$–$C_6$)alkoxy, phenyl($C_1$–$C_6$)alkoxy, ($C_1$–$C_6$) alkylamino, di(($C_1$–$C_6$)alkyl)amino, phenyl($C_1$–$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; and a heterocyclic(($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl;

$R_3$ may also be a group —CR$_a$R$_b$R$_c$ in which:

each of R$_a$, R$_b$ and R$_c$ is independently hydrogen, ($C_1$–$C_6$) alkyl, ($C_2$–$C_6$)alkenyl, ($C_2$–$C_6$)alkynyl, phenyl($C_1$–$C_6$) alkyl, ($C_3$–$C_8$)cycloalkyl, the foregoing being subject to the proviso that R$_a$, R$_b$ and R$_c$ are not all hydrogen; or R$_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring (for example adamantyl); or R$_a$ and R$_b$ are each independently ($C_1$–$C_6$)alkyl, ($C_2$–$C_6$) alkenyl, ($C_2$–$C_6$)alkynyl, phenyl($C_1$–$C_6$)alkyl, or a group as defined for R$_c$ below other than hydrogen, or R$_a$ and R$_b$ together with the carbon atom to which they are attached form a 3 to 8 membered cycloalkyl or a 3- to 8-membered heterocyclic ring, and R$_c$ is hydrogen, —OH, —SH, halogen, —CN, —CO$_2$H, ($C_1$–$C_4$) perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_6$) alkyl, —SO($C_1$–$C_6$)alkyl, —SO$_2$($C_1$–$C_6$) alkyl, —S($C_2$–$C_6$)alkenyl, —SO($C_2$–$C_6$)alkenyl, —SO$_2$ ($C_2$–$C_6$)alkenyl or a group —Q—W wherein Q represents a bond or —O—, —S—, —SO— or —SO$_2$— and W represents a phenyl, phenylalkyl, ($C_3$–$C_8$) cycloalkyl, ($C_3$–$C_8$)cycloalkylalkyl, ($C_4$–$C_8$) cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$–$C_6$)alkyl, —CONH$_2$, —CONH ($C_1$–$C_6$)alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$($C_1$–$C_6$) alkyl, —NO$_2$, —NH$_2$, —NH($C_1$–$C_6$)alkyl, —N( $(C_1-C_6)$alkyl$)_2$, —NHCO$(C_1-C_6)$alkyl, $(C_1-C_6)$alkyl, $(C_2-C_6)$alkenyl, $(C_2-C_6)$alkynyl, $(C_3-C_8)$cycloalkyl, $(C_4-C_8)$cycloalkenyl, phenyl or benzyl.

More specifically with respect to the groups $R_1$, $R_2$, $R_3$, $R_4$ and $R_5$ in compounds of the invention:

Examples of particular $R_2$ groups include iso-butyl, n-pentyl, n-hexyl, n-heptyl, n-octyl, n-nonyl, n-decyl, cyclohexylpropyl, phenylpropyl, phenylpropenyl, 4-chlorophenylpropyl, 4-methylphenylpropyl, 4-methoxyphenylpropyl, pyridine- 4-ylpropyl, phenylbutyl, benzyloxybutyl, propyloxymethyl and propylsulphanyl. Presently preferred are compounds in which $R_2$ is isobutyl, n-octyl, n-decyl, phenylpropyl, benzyloxybutyl, or phenylpropenyl.

Examples of particular $R_3$ groups include benzyl, iso-butyl or t-butyl, 1-benzylthio-1-methylethyl, 1-hydroxy-1-methyl and 1-mercapto-1-methylethyl. Presently preferred are compounds in which $R_3$ is t-butyl or 1-mercapto-1-methylethyl.

$R_4$ is a group —CHR$^x$R$^y$, and examples of R$^x$ and R$^y$ groups include optionally substituted phenyl, thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl. Examples of particular R$^x$ and R$^y$ groups include phenyl, 2-fluorophenyl, 4-fluorophenyl, 2-pyridyl and 4-chlorophenyl. Also the R$^x$ and R$^y$ groups may be linked covalently to each other by a bond or by a $C_1-C_4$ alkylene or $C_2-C_4$ alkenylene bridge, and examples of such linked R$^x$ and R$^y$ groups include the case where $R_4$ is an optionally substituted 9-H-fluoren-9-yl group.

Examples of particular $R_5$ groups include hydrogen, methyl and ethyl. Presently preferred are compounds in which $R_5$ is hydrogen.

Specific examples of compounds of the present invention are:

$N^1$-[1S-(Benzhydryl-carbamoyl)-2,2-dimethyl-propyl]-2R-decyl-succinamide;

3R-[1S-(Benzhydryl-carbamoyl)-2,2-dimethyl-propyl-carbamoyl]-undecanoic acid;

3R-[1S-(Benzhydryl-carbamoyl)-2,2-dimethyl-propyl-carbamoyl]-pentadecanoic acid;

3R-[1S-(Benzhydryl-carbamoyl)-2,2-dimethylpropylcarbamoyl]-7-benzyloxy-heptanoic acid;

$N^1$-[1S-(Benzhydryl-carbamoyl)-2,2-dimethyl-propyl]-2R-decyl-$N^4$-hydroxy-succinamide;

$N^1$-[1S-(Benzhydryl-carbamoyl)-2,2-dimethyl-propyl]-$N^4$-hydroxy-2R-octyl-succinamide;

$N^1$-[1S-(Benzhydryl-carbamoyl)-2,2-dimethyl-propyl]-2R-dodecyl-$N^4$-hydroxy-succinamide;

$N^1$-[1S-(Benzhydryl-carbamoyl)-2,2-dimethyl-propyl]-2R-(4-benzyloxybutyl)-$N^4$-hydroxy-succinamide;

and salts, solvates or hydrates thereof.

Compounds according to the present invention in which X is a hydroxamic acid group —CONHOH may be prepared from corresponding compounds of the invention in which X is a carboxylic acid group —COOH or from the corresponding protected hydroxamic acid derivatives. That process, which forms another aspect of the invention, comprises:

(a) causing an acid of general formula (II)

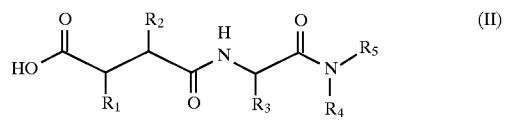

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$ (b) deprotecting a diprotected hydroxamic acid derivative of formula (IIb)

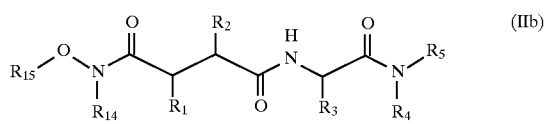

in which $R_1$, $R_2$, $R_3$, $R_4$, and $R_5$ are as defined in general formula (I), $R_{14}$ is an amino protecting group and $R_{15}$ is a hydroxyl protecting group.

For method (a) conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of N,O-diprotected hydroxylamines for use in method (a) above include N,O-bis(benzyl)hydroxylamine, N,O-bis(4-methoxybenzyl)hydroxylamine, N-tert-butoxycarbonyl-O-tert-butyidimethylsilylhydroxylamine, N-tert-butoxycarbonyl-O-tetrahydropyranylhydroxylamine, and N,O-bis(tert-butoxycarbonyl)hydroxylamine.

For method (b) suitable protecting groups $R_{14}$ and $R_{15}$ are benzyl and substituted benzyl (eg 4-methoxybenzyl). Such protecting groups may be removed by hydrogenolysis, while the 4-methoxybenzyl group may also be removed by acid hydrolysis.

In method (a) in the special case where $R_1$ in compound (I) is hydroxy, a particularly useful technique may be reaction of hydroxylamine with a dioxalone of formula (IIa):

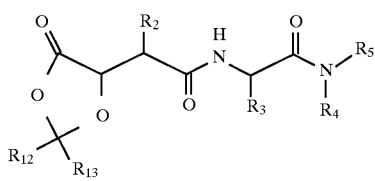

(IIa)

wherein the groups $R_{12}$ and $R_{13}$ are derived from a dioxalone forming reagent, and may be, for example, hydrogen, alkyl, phenyl or substituted phenyl. The dioxalone ring is opened on reaction with hydroxylamine to give the required hydroxamic acid derivative of formula (I).

Compounds according to the present invention in which X is a carboxylic acid group —COOH may be prepared by a process comprising: coupling an acid of formula (III) or an activated derivative thereof with an amine of formula (IV)

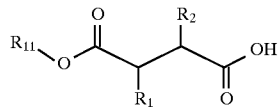

(III)

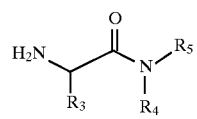

(IV)

wherein $R_1$ $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$ $R_2$, $R_3$, $R_4$, and $R_5$.

Compounds of formula (IIb) may be prepared by a process comprising: causing an acid of formula (IIIa) or an activated derivative thereof to react with an amine of formula (IV)

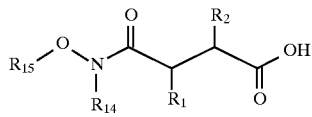

(IIIa)

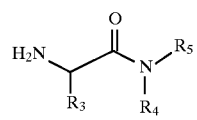

(IV)

wherein $R_1$ $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, $R_{14}$ is an amino protecting group and $R_{15}$ is a hydroxyl protecting group as referred to in connection with formula (IIb) above, and subsequently removing any protecting groups from $R_1$ $R_2$, $R_3$, $R_4$, and $R_5$.

Active derivatives of acids (III) and (IIIa) include activated esters such as the pentafluorophenyl ester, acid anhydrides and acid halides, eg chlorides. Suitable hydroxy protecting groups $R_{11}$ may be selected from those known in the art.

Amine intermediates of formula (IV) are either known compounds or may be prepared from known amino acid starting materials and amines of formula $HNR_4R_5$ using standard methods. Where these amines $HNR_4R_5$ are not commercially available, they may be prepared in two steps from the corresponding ketones (W. R. Roark et al, Bioorg. Med. Chem. 3, 29–39 (1995)).

In the special case where $R_1$ in compound (III) or (IIIa) is hydroxy, it too may be protected during the coupling of compounds (III) or (IIIa) and (IV). In the case where $R_1$ is hydroxy in compound (III) a particularly useful technique may be simultaneous protection of the two hydroxy groups as a dioxalone of formula (V):

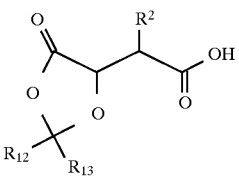

(V)

wherein the groups $R_{12}$ and $R_{13}$ are derived from a dioxalone forming reagent, and may be, for example, hydrogen, alkyl, phenyl or substituted phenyl.

As mentioned above, compounds of formula (I) are useful in human or veterinary medicine since they are active as inhibitors of MMPs, in particular stromelysin and matrilysin.

Accordingly in another aspect, this invention concerns a pharmaceutical or veterinary composition comprising a compound of formula (I) together with a pharmaceutically or veterinarily acceptable excipient or carrier. Included within this aspect of the invention is a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, eg from about 5 to 50 mg of a compound of the invention.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint.

The following Examples illustrate embodiments of the invention:

The amino acids used in the examples were commercially available or were prepared according to literature procedures.

The following abbreviations have been used throughout:
DMF N,N-Dimethylformamide
HOBt 1-Hydroxybenzotriazole
NMM N-Methylmorpholine
TFA Trifluoroacetic acid
EDC N-Ethyl-N'-(3-dimethylaminopropyl)carbodiimide hydrochloride $^1$H and $^{13}$C NMR spectra were recorded using a Bruker AC 250E spectrometer at 250.1 and 62.9 MHz, respectively. Elemental microanalyses were performed by Medac Ltd. (Department of Chemistry, Brunel University, Uxbridge, Middlesex UB8 3PH).

EXAMPLE 1

$N^1$-[1S-(Benzhydryl-carbamoyl)-2,2-dimethyl-propyl]-2R-decyl-succinamide

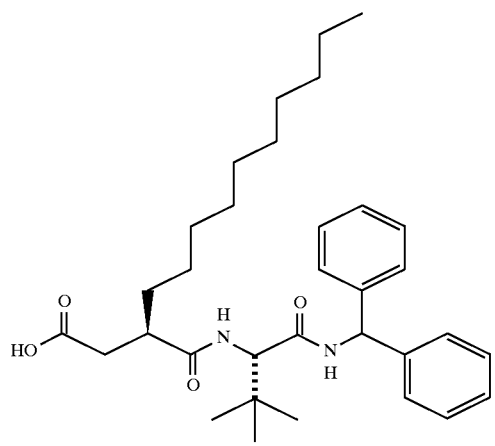

Step A:
$N^\alpha$-Benzyloxycarbonyl-L-tert-leucine-N-benzhydrylamide

To an ice-cooled solution of $N^\alpha$-benzyloxycarbonyl-L-tert-leucine (5.00 g, 18.79 mmol) in DMF (20 ml), was added HOBt (3.04 g, 22.55 mmol) and EDC (4.32 g, 22.55 mmol). The reaction mixture was allowed to warm slowly to room temperature then stirred for 90 minutes at room temperature and cooled back to 0° C. during the addition of aminodiphenylmethane (5.83 ml, 33.82 mmol). The reaction mixture was allowed to warm up to room temperature and was stirred overnight. The solvent was evaporated under reduced pressure and the residue was dissolved in dichloromethane (200 ml). The solution was washed successively with 1N HCl (200 ml) and 1N Na$_2$CO$_3$ (200 ml). The organic phase was separated, dried over anhydrous MgSO$_4$, filtered and concentrated to a yellow oil. The crude product was purified by column chromatography (silica gel, 25% ethyl acetate in hexane) to give the title compound as a white solid (7.43 g, 92%). $^1$H-NMR; δ (CDCl$_3$): 7.38–7.18 (15H, m), 6.74 (1H, d), 6.24 (1H, d, J=7.9 Hz), 5.56 (1H, d, J=9.3 Hz), 5.00, 4.96 (2H, AB, J$_{AB}$=12.2 Hz), 4.08 (1H, d, J=9.5 Hz) and 0.99 (9H, s).

Step B:
L-tert-leucine-N-benzhydrylamide

To a solution of $N^\alpha$-benzyloxycarbonyl-L-tert-leucine-N-benzhydrylamide (7.43 g, 17.27 mmol) in ethanol (100 ml), a slurry of 10% palladium on activated charcoal (0.74 g) in ethyl acetate was added under an atmosphere of argon. Hydrogen gas was bubbled through the reaction mixture for 2 hours. The catalyst was removed by filtration and the solvent was evaporated under reduced pressure to give the desired product as a white solid (5.18 g, 85%). $^1$H-NMR; δ (CDCl$_3$): 7.59 (1H, d, J=7.7 Hz), 7.36 (10H, m), 6.27 (1H, d, J=8.5 Hz), 3.17 (1H, s), 1.51 (2H, br s) and 1.00 (9H, s).

Step C:
3R-[1S-(Benzhydryl-carbamoyl)-2,2-dimethyl-propylcarbamoyl]-tridecanoic acid tert-butyl ester L-tert-leucine-N-benzhydrylamide (1.45 g, 4.83 mmol) was added at 0° C. to a solution of 2R-decyl-succinic acid 4-tert-butyl ester 1-(2, 3, 4, 5, 6-pentafluorophenyl) ester (prepared by a method analogous to that described in WO 92/13831, substituting dodecanoyl chloride for 4-methylpentanoyl chloride) (2.30 g, 4.83 mmol) in DMF (50 ml). The reaction mixture was allowed to warm up to room temperature and was stirred overnight. The solvent was removed under reduced pressure and the residue was dissolved in ethyl acetate (100 ml). The solution was washed with 1N HCl (100 ml) and 1M Na$_2$CO$_3$ (100 ml), dried over anhydrous MgSO$_4$, filtered and concentrated to a yellow oil. The residue was purified by column chromatography (silica gel, 33% ethyl acetate in hexane) to give the product as a colourless oil (1.92 g, 67%). $^1$H-NMR; δ (CDCl$_3$), 7.36–7.17 (10H, m), 6.60 (1H, d, J=8.1 Hz), 6.42 (1H, d, J=9.2 Hz), 6.23 (1H, d, J=8.0 Hz), 4.32 (1H, d, J=9.3 Hz), 2.62 (2H, m), 2.35–2.24 (1H, m), 1.42 (9H, s), 1.34–1.15 (18H, m), 0.99 (9H, s), 0.90 (3H, d, J=6.3 Hz) and 0.88 (3H, d, J=6.8 Hz).

Step D:
3R-[1S-(Benzhydryl-carbamoyl)-2,2-dimethyl-propylcarbamoyl]-tridecanoic acid To a solution of 3R-[1S-(benzhydryl-carbamoyl)-2,2-dimethyl-propylcarbamoyl]-tridecanoic acid tert-butyl ester (2.28 g, 3.81 mmol) in dichloromethane (10 ml) was added TFA (10 ml). The reaction mixture was allowed to stand in the refrigerator (4° C.) overnight. The solvent was removed under reduced pressure and toluene (50 ml) was added. The solvent was removed under reduced pressure and the residue was azeotroped with toluene four more times. The residue was chromatographed (silica gel, 50% ethyl acetate in hexane) to give the title compound as a colourless oil (2.08 g, 98%). $^1$H-NMR; δ (CDCl$_3$), 7.47 (1H, d, J=8.4 Hz), 7.35–7.12 (10H, m), 7.03 (1H, d, J=9.5 Hz), 6.25 (1H, d, J=8.2 Hz), 4.56 (1H, d, J=9.5 Hz), 2.64–2.55 (2H, m), 2.27 (1H, d, J=13.7 Hz), 1.48–1.13 (18H, m) and 0.92–0.86 (12H, m). $^{13}$C-NMR; δ (CDCl$_3$), 176.0, 175.4, 170.6, 141.2, 140.6, 128.6, 128.5, 127.9, 127.6, 127.2, 126.8, 60.4, 56.9, 42.5, 36.0, 34.9, 34.8, 32.5, 31.9, 31.0, 29.6, 29.5, 29.4, 29.3, 29.2, 27.2, 26.5, 22.7 and 14.1. IR; ν$_{max}$ (KBr), 2922, 1711, 1656 and 1504 cm$^{-1}$. Found: C 73.69, H 9.04, N 5.13%; C$_{33}$H$_{48}$N$_2$O$_4$ requires: C 73.84, H 9.01, N 5.22%.

The following additional compounds were prepared according to the methods of Example 1:

EXAMPLE 2

3R-[1S-(Benzhydryl-carbamoyl)-2,2-dimethyl-propyl-carbamoyl]-undecanoic acid

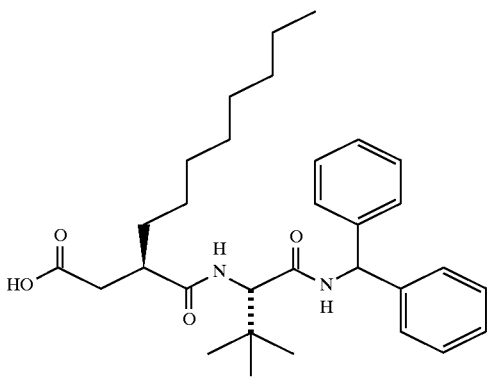

White foam. $^1$H-NMR; δ (CDCl$_3$), 7.61 (1H, d, J=8.3 Hz), 7.35–7.05 (11H, m), 6.26 (1H, d, J=8.2 Hz), 4.60 (1H, d, J=9.7 Hz), 2.62–2.53 (2H, m), 2.26–2.21 (1H, m), 1.29–1.21 (14H, m) and 1.11–0.85 (12H, m), $^{13}$C-NMR; δ (CDCl$_3$), 175.8, 175.2, 170.4, 141.3, 140.8, 128.6, 128.5, 127.9, 127.6, 127.2, 127.0, 60.4, 56.9, 42.5, 36.1, 34.7, 32.5, 31.8, 29.5, 29.4, 29.3, 27.2, 26.6, 22.6 and 14.1. IR; ν$_{max}$ (CDCl$_3$), 2924, 1712, 1659 and 1498 cm$^{-1}$. Found: 73.19, H 8.72, N 5.48%; C$_{31}$H$_{44}$N$_2$O$_4$ requires: C 73.19, H 8.72, N 5.51%.

EXAMPLE 3

3R-[1S-(Benzhydryl-carbamoyl)-2,2-dimethyl-propyl-carbamoyl]-pentadecanoic acid

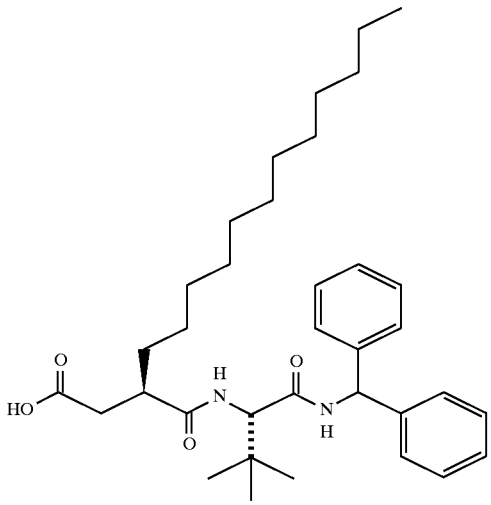

White foam. $^1$H-NMR; δ (CDCl$_3$), 7.56 (1H, d, J=8.1 Hz), 7.37–7.12 (10H, m), 7.06 (1H, d, J=9.7 Hz), 6.26 (1H, d, J=8.3 Hz), 4.59 (1H, d, J=9.8 Hz), 2.54 (2H, m), 2.25 (1 H, m), 1.37–1.12 (22H, m) and 0.92–0.67 (12H, m). $^{13}$C—NMR; δ (CDCl$_3$), 175.8, 175.3, 170.4, 141.3, 140.8, 128.7, 128.5, 127.9, 127.6, 127.2, 127.0, 60.4, 56.8, 42.5, 36.1, 34.8, 32.5, 31.9, 29.7, 29.5 (2s), 29.4, 27.2, 26.6, 22.7 and 14.1. IR; ν$_{max}$ (KBr), 2919, 2853, 1713, 1651 and 1497 cm$^{-1}$. Found: C 74.19, H 9.31, N 4.92%; C$_{35}$H$_{52}$N$_2$O$_4$ requires: C 74.43, H 9.28, N 4.96%.

EXAMPLE 4

3R-[1S-(Benzhydryl-carbamoyl)-2,2-dimethylpropylcarbamoyl]-7-benzyloxy-heptanoic acid

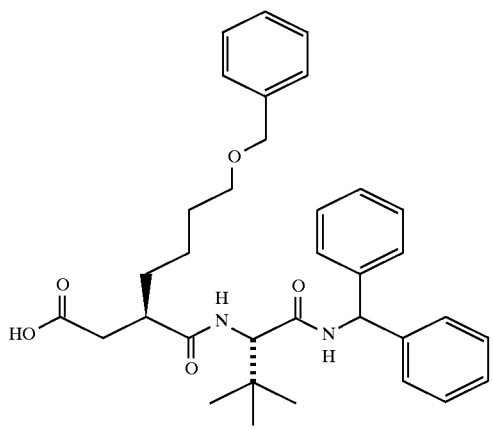

White solid. $^1$H-NMR; δ (CDCl$_3$), 7.27 (15H, m), 6.83 (2H, m), 6.22 (1H, d, J=8.1 Hz), 4.44 (2H, s), 4.40 (1H, d, J=9.6 Hz), 3.33 (2H, t, J=6.6 Hz), 2.64 (2H, m), 2.40 (1H, d, J=13.5 Hz), 1.52 (3H, m), 1.29 (3H, m) and 0.95 (9H, s). $^{13}$C-NMR; δ (CDCl$_3$), 175.3, 175.0, 170.0, 141.7, 138.5, 128.7, 128.6, 128.4, 127.7, 127.5, 127.4, 127.0, 72.8, 69.9, 60.7, 57.0, 42.3, 36.3, 34.8, 32.1, 29.3, 26.5 and 23.7.

The starting material, 2R-benzyloxybutylsuccinic acid 4-tert-butyl ester, was prepared according to a literature procedure (M. R. Gowravaram et al., J. Med. Chem, 1995, 38: 2570–2581).

EXAMPLE 5

N$^1$-[1S-(Benzhydryl-carbamoyl)-2,2-dimethyl-propyl]-2R-decyl-N$^4$-hydroxy-succinamide

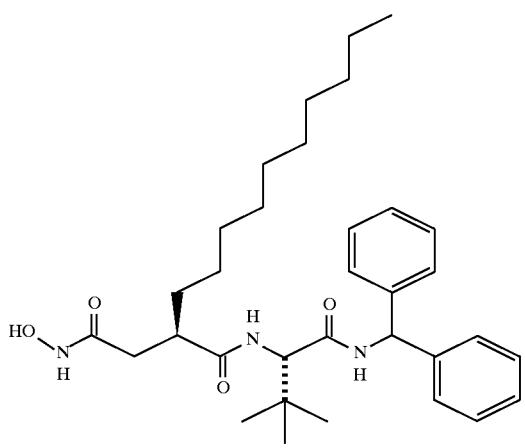

Step A:
N$^1$-[1S-(Benzhydryl-carbamoyl)-2,2-dimethyl-propyl]-N$^4$-benzyloxy-2R-decyl-succinamide 3R-[1S-(Benzhydryl-carbamoyl)-2,2-dimethyl-propylcarbamoyl]-tridecanoic acid (Example 1) (1.80 g, 3.38 mmol) was dissolved in DMF (50 ml) and cooled to 0° C. during the addition of HOBt (0.68 g, 5.07 mmol) and EDC (0.97 g, 5.07 mmol). The reaction mixture was allowed to warm up to room temperature and was stirred for 6 hours. O-Benzylhydroxylamine (0.83 g, 6.76 mmol) was added to the reaction mixture, which was then allowed to stir overnight. The solvent was removed under reduced pressure and the residual oil was dissolved in dichloromethane (100 ml) and washed with water (2×100 ml). The organic phase was separated, dried over anhydrous MgSO$_4$, filtered and concentrated to a yellow oil. The crude product was purified by column chromatography (silica gel, gradient elution, 33% to 50% ethyl acetate in hexane) to give the product as a white foam (0.61 g, 28%). $^1$H-NMR; δ (CDCl$_3$), 9.18 (1H, s), 7.51–7.14 (16H, m), 6.93 (1H, d, J=9.7 Hz), 6.18 (1H, d, J=8.3 Hz), 4.75 (2H, s), 4.42 (1H, d, J=9.7 Hz), 2.98–2.85 (1H, m), 2.35–2.10 (2H, m), 1.60–1.03 (18H, m), 0.97 (9H, s) and 0.90 (3H, d, J=6.3 Hz), 0.88 (3H, d, J=6.3 Hz).
Step B:
N$^1$-[1S-(Benzhydryl-carbamoyl)-2,2-dimethyl-propyl]-2R-decyl-N$^4$-hydroxy-succinamide To a solution of N$^1$-[1-(benzhydryl-carbamoyl)-2,2-dimethyl-propyl]-N$^4$-benzyloxy-2-decyl-succinamide (0.60 g, 0.94 mmol) in ethanol (30 ml), a slurry of 15% palladium on activated charcoal (90 mg) in ethyl acetate was added, under an argon atmosphere. Hydrogen gas was bubbled through the reaction mixture for two hours and the reaction mixture was stirred under positive pressure of hydrogen overnight. The catalyst was removed by filtration and the solvent was evaporated under reduced pressure. The residue was suspended in ether and the solvent was removed under reduced pressure to give the desired product as a white solid (0.32 g, 61%). m.p. 164.5° C. $^1$H-NMR; δ (CD$_3$OD), 8.77 (1H, d, J=8.4Hz), 7.74 (1H, d, J=9.3 Hz), 7.12 (10H, m), 6.09 (2H, d, J=8.4 Hz), 4.31 (1H, d, J=9.4 Hz), 2.72 (1H, m), 2.25 (1H, m), 2.05 (1H, m), 1.50–1.05 (18H, m), 0.86 (9H, s) and 0.79 (3H, t, J=6.6 Hz). $^{13}$C—NMR; δ (CD$_3$OD), 177.0, 171.8, 170.6, 142.8, 142.8, 129.5, 129.3, 129.1, 128.4, 128.1, 61.9, 57.9, 43.8, 36.6, 35.5, 33.6, 33.0, 30.7, 30.5, 30.4, 28.2, 27.1, 23.7 and 14.4. IR; v$_{max}$ (KBr), 2928, 1644, 1538, 1368, 1193 and 698 cm$^{-1}$. Found: C 68.71, H 8.94, N 7.62%; C$_{33}$H$_{49}$N$_3$O$_4$. 1.4H$_2$O requires: C 68.69, H 9.05, N 7.28%.

The following additional compounds were prepared according to the methods of Example 5:

EXAMPLE 6

N$^1$-[1S-(Benzhydryl-carbamoyl)-2,2-dimethyl-propyl]-N$^4$-hydroxy-2R-octyl-succinamide

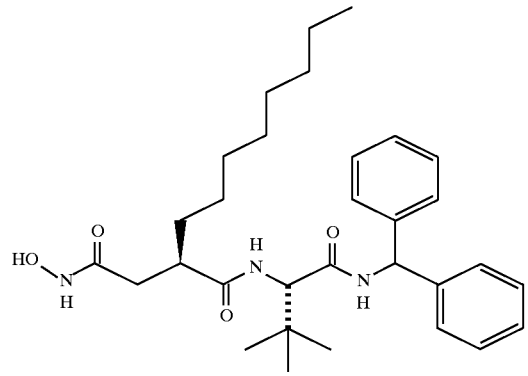

White foam. $^1$H-NMR; δ (CD$_3$OD), 8.77 (1H, d, J=8.6 Hz), 7.25–7.08 (10H, m), 6.10 (1H, s), 4.32 (1H, s), 2.77–2.68 (1H, m), 2.29–2.03 (2H, m), 1.46–1.00 (14H, m), 0.86 (9H, s) and 0.78 (3H, t, J=6.6 Hz). $^{13}$C—NMR; δ (CD$_3$OD), 177.0, 171.8, 170.6, 142.9, 142.8, 129.5, 129.3, 129.1, 128.4, 128.4, 128.1, 61.9, 57.9, 43.8, 36.6, 35.5, 33.6, 33.0, 30.7, 30.5, 30.4, 28.2, 27.1, 23.6 and 14.4. IR; v$_{max}$ (KBr), 3281, 2821, 1643, 1534 and 697 cm$^{-1}$. Found: C 70.90, H 8.59, N 7.98%; C$_{31}$H$_{45}$N$_3$O$_4$ requires: C 71.10, H 8.66, N 8.02%.

EXAMPLE 7

$N^1$-[1S-(Benzhydryl-carbamoyl)-2,2-dimethyl-propyl]-2R-dodecyl-$N^4$-hydroxy-succinamide

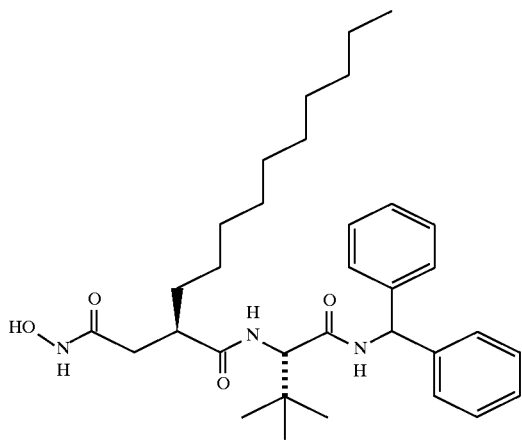

White foam. $^1$H-NMR; δ (CD$_3$OD), 7.24–7.08 (10H, m), 6.10 (1H, s), 4.32 (1H, s), 2.74–2.69 (1H, m), 2.29–2.03 (2H, m), 1.46–0.94 (22H, m), 0.87 (9H, s) and 0.79 (3H, t, J=6.5 Hz). $^{13}$C—NMR; δ (CD$_3$OD), 177.0, 171.8, 170.6, 142.8, 142.8, 129.5, 129.3, 129.1, 128.4, 128.1, 61.9, 57.9, 43.8, 36.6, 35.5, 33.6, 33.0, 30.7, 30.5, 30.4, 28.2, 27.1, 23.7 and 14.4. IR; $v_{max}$ (KBr),2922, 1639, 1533 and 694 cm$^{-1}$. Found: C 72.22, H 9.21, N 7.28%; $C_{35}H_{53}N_3O_4$ requires: C 72.50, H 9.21, N 7.25%.

EXAMPLE 8

$N^1$-[1S-(Benzhydryl-carbamoyl)-2,2-dimethyl-propyl]-2R-(4-benzyloxybutyl)-$N^4$-hydroxy-succinamide

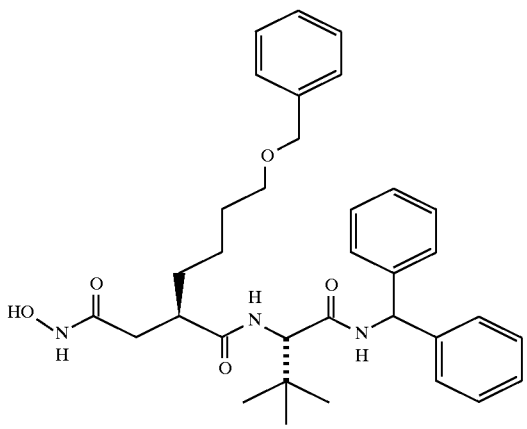

White solid. m.p. 146°–147° C. $^1$H-NMR; δ (CD$_3$OD), 7.19 (15H, m), 6.08 (1H, t, J=4.5 Hz), 4.30 (3H, s), 3.21 (2H, t, J=6.7 Hz), 2.74 (1H, m), 2.24 (1H, dd, J=8.0, 14.5 Hz), 2.07 (1H, dd, J=6.5, 14.6 Hz), 1.41 (4H, m), 1.27 (2H, m) and 0.87 (9H, s). ($^{13}$C-NMR; δ (CD$_3$OD), 171.9, 170.7, 142.9 (2s), 139.9, 137.4, 131.8, 129.6, 129.5, 129.4, 129.1, 128.8, 128.6, 128.5, 128.2, 73.8, 71.2, 62.1, 58.0, 43.7, 36.6, 35.5, 33.4, 30.6, 27.2 and 24.8.

We claim:
1. A compound of formula I

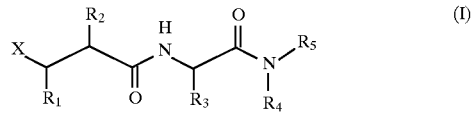

wherein

X is a —CO$_2$H or —CONHOH group;

$R_1$ is hydrogen;

$R_2$ is a (C$_1$–C$_6$)alkyl, (C$_2$–C$_6$)alkenyl, (C$_2$–C$_6$)alkynyl, phenyl(C$_1$–C$_6$)alkyl, heteroaryl(C$_1$–C$_6$)alkyl, cycloalkyl(C$_1$–C$_6$)alkyl or cycloalkenyl(C$_1$–C$_6$) alkyl group, any one of which may be optionally substituted by one or more substituents selected from (C$_1$–C$_6$) alkyl, —O(C$_1$–C$_6$)alkyl, —S(C$_1$–C$_6$)alkyl, —OCH$_2$Ph wherein the phenyl group may be optionally substituted, halo and cyano (—CN);

$R_3$ is the characterising group of a natural or non-natural α amino acid in which any functional groups may be protected;

$R_4$ is a group —CHR$^x$R$^y$ wherein R$_x$ and R$^y$ independently represent optionally substituted phenyl or monocyclic heteroaryl rings, which optionally may be linked covalently to each other by a bond or by a C$_1$–C$_4$ alkylene or C$_2$–C$_4$ alkenylene bridge, either of which may be optionally interrupted by an O or S atom;

$R_5$ is hydrogen or a (C$_1$–C$_6$)alkyl group;

or a salt, hydrate or solvate thereof.

2. A compound as claimed in claim 1 wherein the stereochemistry is as follows:

C atom carrying the $R_1$ and X groups—S,

C atom carrying the $R_2$ group—R,

C atom carrying the $R_3$ group—S,

C atom carrying the R$^x$ and R$^y$ groups—R or S.

3. A compound as claimed in any one of the preceding claims wherein $R_2$ is iso-butyl, n-pentyl, n-hexyl, n-heptyl, n-octyl, n-nonyl, n-decyl, cyclohexylpropyl, phenylpropyl, phenylpropenyl, 4-chlorophenylpropyl, 4-methylphenylpropyl, 4-methoxyphenylpropyl, pyridine-4-ylpropyl, phenylbutyl, benzyloxybutyl, propyloxymethyl or propylsulphanyl.

4. A compound as claimed in any one of the preceding claims wherein $R_3$ is:

(C$_1$–C$_6$)alkyl, benzyl, hydroxybenzyl, benzyloxybenzyl, (C$_1$–C$_6$)alkoxybenzyl, or benzyloxy(C$_1$–C$_6$)alkyl group; or the characterising group of a natural α amino acid, in which any functional group may be protected, any amino group may be acylated and any carboxyl group present may be amidated; or a group —[Alk]$_n$R$_6$ where Alk is a (C$_1$–C$_6$)alkyl or (C$_2$–C$_6$)alkenyl group optionally interrupted by one or more —O—, or —S— atoms or —N(R$_7$)— groups, n is 0 or 1, and R$_6$ is an optionally substituted cycloalkyl or cycloalkenyl group; or a benzyl group substituted in the phenyl ring by a group of formula —OCH$_2$COR$_8$ where R$_8$ is hydroxyl, amino, (C$_1$–C$_6$)alkoxy, phenyl(C$_1$–C$_6$)alkoxy, (C$_1$–C$_6$) alkylamino, di((C$_1$–C$_6$)alkyl)amino, phenyl(C$_1$–C$_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or a heterocyclic(($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl.

5. A compound as claimed in any one of claims 1 to 3 wherein $R_3$ is a group $CR_aR_bR_c$ in which:

each of $R_a$, $R_b$ and $R_c$ is independently hydrogen, ($C_1$–$C_6$) alkyl, ($C_2$–$C_6$)alkenyl, ($C_2$–$C_6$)alkynyl, phenyl($C_1$–$C_6$) alkyl, ($C_3$–$C_8$)cycloalkyl, the foregoing being subject to the proviso that $R_a$, $R_b$ and $R_c$ are not all hydrogen; or $R_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$) alkenyl, ($C_2$–$C_6$)alkynyl, phenyl($C_1$–$C_6$)alkyl, or a group as defined for $R_c$ below other than hydrogen, or $R_a$ and $R_b$ together with the carbon atom to which they are attached form a 3 to 8 membered cycloalkyl or a 3- to 8-membered heterocyclic ring, and $R_c$ is hydrogen, —OH, —SH, halogen, —CN, —$CO_2H$, ($C_1$–$C_4$) perfluoroalkyl, —$CH_2OH$, —$CO_2$($C_1$–$C_6$)alkyl, —O($C_1$–$C_6$)alkyl, —O($C_2$–$C_6$)alkenyl, —S($C_1$–$C_6$) alkyl, —SO($C_1$–$C_6$)alkyl, —$SO_2$($C_1$–$C_6$)alkyl, —S($C_2$–$C_6$)alkenyl, —SO($C_2$–$C_6$)alkenyl, —$SO_2$ ($C_2$–$C_6$)alkenyl or a group —Q—W wherein Q represents a bond or —O—, —S—, —SO— or —$SO_2$— and W represents a phenyl, phenylalkyl, ($C_3$–$C_8$) cycloalkyl, ($C_3$–$C_8$)cycloalkylalkyl, ($C_4$–$C_8$) cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —$CO_2H$, —$CO_2$($C_1$–$C_6$)alkyl, —$CONH_2$, —CONH ($C_1$–$C_6$)alkyl, —CONH($C_1$–$C_6$alkyl)$_2$, —CHO, —$CH_2OH$, ($C_1$–$C_4$)perfluoroalkyl, —O($C_1$–$C_6$)alkyl, —S($C_1$–$C_6$)alkyl, —SO($C_1$–$C_6$)alkyl, —$SO_2$($C_1$–$C_6$) alkyl, —$NO_2$, —$NH_2$, —NH($C_1$–$C_6$)alkyl, —N( ($C_1$–$C_6$)alkyl)$_2$, —NHCO($C_1$–$C_6$)alkyl, ($C_1$–$C_6$)alkyl, ($C_2$–$C_6$)alkenyl, ($C_2$–$C_6$)alkynyl, ($C_3$–$C_8$)cycloalkyl, ($C_4$–$C_8$)cyloalkenyl, phenyl or benzyl.

6. A compound as claimed in any one of claims 1 to 3 wherein $R_3$ is benzyl, iso-butyl, t-butyl, 1-benzylthio-1-methylethyl, 1-hydroxy-1-methylethyl or 1-mercapto-1-methylethyl.

7. A compound as claimed in any one of the preceding claims wherein $R_4$ is a group —$CHR^xR^y$, in which of $R^x$ and $R^y$ groups are independently selected from optionally substituted phenyl, thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

8. A compound as claimed in claim 7 wherein $R^x$ and $R^y$ are independently phenyl, 2-fluorophenyl, 4-fluorophenyl, 2-pyridyl or 4-chlorophenyl.

9. A compound as claimed in any one of claims 1 to 6 in which $R_4$ is optionally substituted 9-H-fluoren-9-yl.

10. A compound as claimed in any one of the preceding claims in which $R_5$ is hydrogen.

11. A compound selected from the group consisting of;

$N^1$-[1S-(Benzhydryl-carbamoyl)-2,2-dimethyl-propyl]-2R-decyl-succinamide;

3R-[1S-(Benzhydryl-carbamoyl)-2,2-dimethyl-propyl-carbamoyl]-undecanoicacid;

3R-[1S-(Benzhydryl-carbamoyl)-2,2-dimethyl-propyl-carbamoyl]-pentadecanoic acid;

3R-[1S-(Benzhydryl-carbamoyl)-2,2-dimethylpropylcarbamoyl]-7-benzyloxy-heptanoic acid;

$N^1$-[1S-(Benzhydryl-carbamoyl)-2,2-dimethyl-propyl]-2R-decyl-$N^4$-hydroxy-succinamide;

$N^1$-[1S-(Benzhydryl-carbamoyl)-2,2-dimethyl-propyl]-$N^4$-hydroxy-2R-octyl-succinamide;

$N^1$-[1S-(Benzhydryl-carbamoyl)-2,2-dimethyl-propyl]-2R-dodecyl-$N^4$-hydroxy-succinamide;

$N^1$-[1S-(Benzhydryl-carbamoyl)-2,2-dimethyl-propyl]-2R-(4-benzyloxybutyl)-$N^4$-hydroxy-succinamide;

and salts, solvates or hydrates thereof.

12. A process for the preparation of a compound as claimed in claim 1 in which X is a hydroxamic acid group (—CONHOH), which process comprises:

(a) causing an acid of general formula (II)

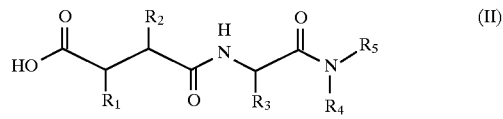

or an activated derivative thereof to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$; or (b) deprotecting a diprotected hydroxamic acid derivative of formula (IIb)

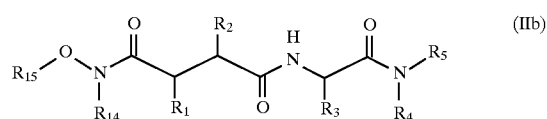

in which $R_1$, $R_2$, $R_3$, $R_4$, and $R_5$ are as defined in general formula (I), $R_{14}$ is an amino protecting group and $R_1$ is a hydroxyl protecting group.

13. A process as claimed in claim 12 wherein in step (a) (in the special case where $R_1$ in compound (I) is hydroxy) the hydroxy group $R_1$ and the adjacent carboxyl group are simultaneously protected as a dioxalone of formula (IIa):

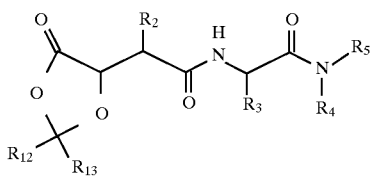

wherein the groups $R_{12}$ and $R_{13}$ are derived from a dioxalone forming reagent, and the dioxalone ring being is opened by the reaction with hydroxylamine to give the required hydroxamic acid derivative of formula (I).

14. A process for the preparation of a compound as claimed in claim 1 in which X is a carboxylic acid group (—COOH) which process comprises coupling an acid of formula (III) or an activated derivative thereof with an amine of formula (IV)

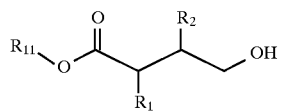

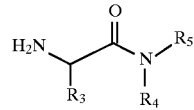

wherein $R_1$ $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$ $R_2$, $R_3$, $R_4$, and $R_5$.

15. A process as claimed in claim 14 wherein (in the special case where $R_1$ in compound (I) is hydroxy) compound (III) has the formula (V):

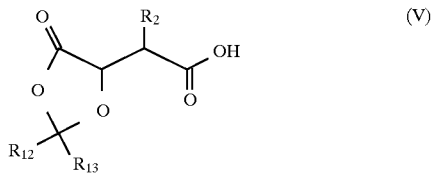

wherein $R_2$ is as defined in general formula (I) and the groups $R_{12}$ and $R_{13}$ are derived from a dioxalone forming reagent.

16. A pharmaceutical or veterinary composition comprising a compound as claimed in any one of claims 1 to 11 together with a pharmaceutically or veterinarily acceptable excipient or carrier.

* * * * *